(12) United States Patent
Dhara et al.

(10) Patent No.: US 10,421,777 B2
(45) Date of Patent: Sep. 24, 2019

(54) PROCESS FOR EXTRACTION OF FISH COLLAGEN AND FORMULATIONS OF 3D MATRICES OF COLLAGEN FOR BIOMEDICAL AND THERAPEUTIC APPLICATIONS THEREOF

(71) Applicant: AMNIVOR MEDICARE PRIVATE LIMITED, Kharagpur (IN)

(72) Inventors: Santanu Dhara, Kolkata (IN); Pallab Majumdar, Howrah (IN); Nilanjana Maiti, Kharagpur (IN)

(73) Assignee: Amnivor Medicare Private Limited, West Bengal, Kharagpur (IN)

( * ) Notice: Subject to any disclaimer, the term of this patent is extended or adjusted under 35 U.S.C. 154(b) by 0 days.

(21) Appl. No.: 15/406,453

(22) Filed: Jan. 13, 2017

(65) Prior Publication Data
US 2017/0204136 A1    Jul. 20, 2017

(30) Foreign Application Priority Data

Jan. 14, 2016   (IN) .............................. 201631001353

(51) Int. Cl.
| | | |
|---|---|---|
| C07K 1/36 | (2006.01) |
| A61K 9/06 | (2006.01) |
| A61K 9/70 | (2006.01) |
| A61K 31/722 | (2006.01) |
| A61K 38/39 | (2006.01) |
| A61L 15/18 | (2006.01) |
| A61L 15/28 | (2006.01) |
| A61L 15/32 | (2006.01) |
| A61L 15/44 | (2006.01) |
| A61L 15/60 | (2006.01) |
| C07K 1/14 | (2006.01) |
| C07K 1/34 | (2006.01) |
| C07K 14/78 | (2006.01) |
| C08B 37/08 | (2006.01) |
| C08L 5/08 | (2006.01) |
| C12M 1/12 | (2006.01) |
| G02B 1/04 | (2006.01) |
| A61K 47/36 | (2006.01) |
| A61L 15/40 | (2006.01) |
| A61L 26/00 | (2006.01) |
| C08L 89/06 | (2006.01) |

(52) U.S. Cl.
CPC ................. *C07K 1/36* (2013.01); *A61K 9/06* (2013.01); *A61K 9/7007* (2013.01); *A61K 31/722* (2013.01); *A61K 38/39* (2013.01); *A61K 47/36* (2013.01); *A61L 15/18* (2013.01); *A61L 15/28* (2013.01); *A61L 15/325* (2013.01); *A61L 15/40* (2013.01); *A61L 15/44* (2013.01); *A61L 15/60* (2013.01); *A61L 26/008* (2013.01); *A61L 26/0057* (2013.01); *C07K 1/145* (2013.01); *C07K 1/34* (2013.01); *C07K 14/78* (2013.01); *C08B 37/003* (2013.01); *C08L 5/08* (2013.01); *C08L 89/06* (2013.01); *C12M 25/14* (2013.01); *G02B 1/043* (2013.01); *A61L 2300/106* (2013.01); *A61L 2300/404* (2013.01)

(58) Field of Classification Search
None
See application file for complete search history.

(56) References Cited

U.S. PATENT DOCUMENTS

2007/0231878 A1   10/2007   Wu et al.

FOREIGN PATENT DOCUMENTS

| CN | 1381274 A | 11/2002 |
|---|---|---|
| CN | 1167471 C | 9/2004 |
| CN | 1814782 | 8/2006 |
| CN | 1888075 A | 1/2007 |

(Continued)

OTHER PUBLICATIONS

Catalina et al., Molecular weight separation of collagen-base biomaterials by ultrafiltration, (2013), available online at: www.researchgate.net/publication/268290508_Molecular_weight_separation_of_collagen-base_biomaterials_by_ultrafiltration.*

(Continued)

*Primary Examiner* — Jennifer M. H. Tichy
(74) *Attorney, Agent, or Firm* — D'Ambrosio & Menon, PLLC; Usha Menon

(57) ABSTRACT

Polyelectrolyte based bioactive super-absorbent material ionotropically crosslinked/neutralized involving polyvalent carboxylic acids, citrate, Kojic Acid, Alpha Arbutin along with fish scale collagen cross linked with other polyelectrolyte biopolymers preferably selected from chitosan, alginate or their combinations is used in this invention. The advancement is also directed to process of extraction of collagen of high purity from fresh water fish scale by salt and alkaline washing, crushing followed by continuous dialysis thereby minimizing the chance of collagen degradation. Also disclosed are different forms of collagen-chitosan composite biomaterial using citrate as the neutralizing buffer in combination with antimicrobial agent, antioxidant, skin plumper and melanin reducer wherein the different forms of collagen chitosan particularly sheet, flakes, powder, gel, particles, fiber, film, spray etc. reveal efficient wound healing properties. The advancement is thus directed to find wide application in various dermal wound healing, tissue engineering, 3D cell culture, cell expansion and cell delivery vehicle, mimicking the in vivo situation in dynamic condition, cosmetics and different other health care applications.

4 Claims, 3 Drawing Sheets

(56) References Cited

FOREIGN PATENT DOCUMENTS

Figure 1:
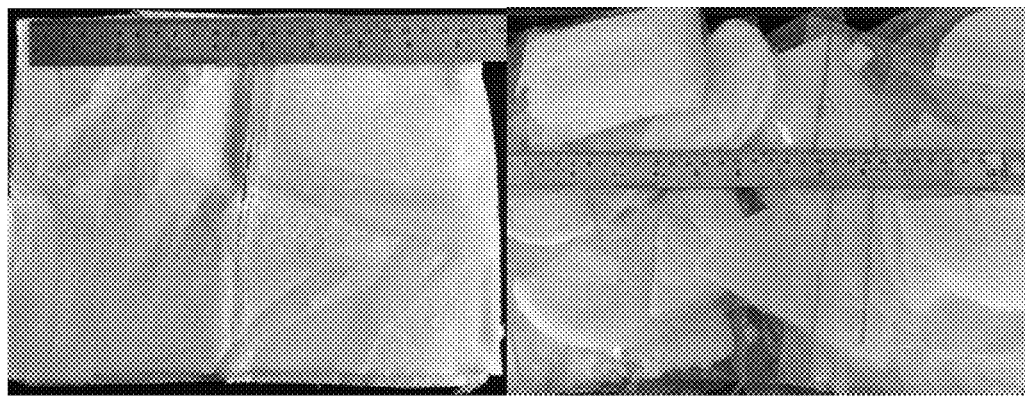

| | | | | |
|---|---|---|---|---|
| CN | 1948411 | * | 4/2007 | ............... A61K 8/65 |
| CN | 1332981 C | | 8/2007 | |
| CN | 103570827 | | 2/2014 | |
| CN | 103773828 | | 5/2014 | |
| CN | 104004086 A | | 8/2014 | |
| EP | 0200574 A2 | | 11/1986 | |
| EP | 1115432 A1 | | 7/2001 | |

OTHER PUBLICATIONS

K.A. Piez, et al., Biochemistry, "The Nature and Location of Intramolecular Cross Links in Collagen;" Dec. 1965; 4(12):2590-2596.

T.H. Silva, et.al. "Marine Origin Collagens and Its Potential Applications" Mar. Drugs 2014, 12, 5881-5901.

T. Nagai, et.al., "Collagen of edible jellyfish exumbrella" J Sci Food Agric 79:855-858;1999.

B. Wang, et al. "Isolation and Characterization of Collagen and Antioxidant Collagen Peptides from Scales of Croceine Croaker" Mar. Drugs 2013, 11, 4641-4661.

Pati, B. Adhikari, S. Dhara, Isolation and characterization of fish scale collagen of higher thermal stability, Bioresource Technology, 101, 3737-3742, 2010.

National Biodiversity Authority, India, The Biological Diversity Act, 2002.†

\* cited by examiner
† cited by third party

PROCESS FOR EXTRACTION OF FISH COLLAGEN AND FORMULATIONS OF 3D MATRICES OF COLLAGEN FOR BIOMEDICAL AND THERAPEUTIC APPLICATIONS THEREOF

CROSS-REFERENCE TO RELATED APPLICATIONS

This application is related to and claims priority to Indian Patent Application No. 201631001353 filed on Jan. 14, 2016, the contents of which are incorporated by reference herein.

FIELD OF THE INVENTION

The present invention relates to a process for extraction of collagen from fish scale a polyelectrolyte based bioactive super-absorbent material. More specifically, the present invention provides the process for extraction of collagen of high purity from fish scale and the manufacture of polyelectrolyte based bioactive super-absorbent material such as chitosan-collagen based composite biomaterial. Advantageously, the polyelectrolyte based bioactive super-absorbent material of the advancement is found to have efficient wound healing property and thus finds beneficial application in dermal wound dressing and other health care applications like tissue engineering scaffolds, drug delivery system, cell delivery vehicles, cell culture system and transient 3D matrix for cell expansion. 3D forms of polyelectrolyte based bioactive super-absorbent materials is found to be used in biomedical, therapeutic and dynamic cell culture applications, and mimics the in vivo situation in cytotoxicity, drugs and other in vivo assessments.

BACKGROUND ART

Collagen is the most abundant protein representing nearly 30% of total proteins in the animal body. It is the major component of extracellular matrices and is vital for mechanical protection of tissues, organs, and physiological regulation of cellular environment. Collagen and collagen based forms in combination with other synthetic, semi-synthetic and biopolymers have broad applications in wound healing, tissue engineering, regenerative medicine, moisturiser, food industry, laboratory reagents, health drink, etc.

Aquatic source of collagen is of great importance worldwide. Marine source of Type I collagen are fishes such as codfish [K. A. Piez, *Biochemistry,* 1965 December; 4(12): 2590-2596], salmon, skin of Big eye snapper, Large fin long barbel catfish, Cuttlefish, scales of Lizard fish, Horse mackerel, Grey mullet, Flying fish, Yellowback seabream etc. [T. H. Silva, et. al. Mar. Drugs 2014, 12, 5881-5901], or invertebrate marine animals, such as marine sponges, star fish, octopus or jellyfish [T. Nagai, et. al., J Sci Food Agric 79:855-858; 1999]. The marine sources contains higher amount of minerals and therefore, removing of them is costly, time consuming and cumbersome and usually ethylenediaminetetraacetic acid (EDTA) is used for this. However, remnant EDTA in collagen to be used for medical devices is very harmful for skeletal tissues and can cause to decay of bones.

Further, the denaturation temperature ($T_d$) of collagen from marine source is low. The denaturation temperature ($T_d$) of edible jelly fish collagen is 26.0° C. [T. Nagai, J Sci Food Agric 79:855-858, 1999] and that of starfish is 24.7° C. [B. Wang, Mar. Drugs 2013, 11, 4641-4661].

The mineral content in fresh water fish scale is relatively less. Moreover, this source is free from the fat or turbid matter. The scales and other external part of fish, considered to be biological wastes, are rich sources of collagen. The extraction procedure of collagen from theses sources is simple, less time consuming and can be extracted using less chemical treatments. This collagen of fresh water origin has relatively higher denaturation temperature ($T_d$) mainly due to high content of hydroxyproline associated with nature of their habitat.

It is well known that the extraction of collagen from fish scale usually comprises either of the enzymatic method/hot water extraction method/methanol/EDTA or a combination of them.

CN 103773828 discloses method for extraction of collagen from fish scale by conducting crushing, hot water and enzymatic treatment using 1-3% of protease assisted by ultrasonic wave. Without acid-base pre-treatment, the method provided has no pollution to the environment, can achieve good separation and purification effect, and does not affect the biological activity of collagen.

CN 1814782, mentions an enzyme engineering technology including taking scales as the main raw material, drying and crushing them to be sieved, mixed with water, enzymolyzed with proteinases then to eliminate; enzymes and filter them to get the solution to be concentrated, dried to get the product and extracting small molecular collagens from the scales by a biological enzyme cutting technology where hydrolysis is carried out at 35-70° C. for 3 to 12 hours followed by heating reaction liquid at 90° C. for constant temperature enzyme inactivation.

CN 103570827 discloses preparation methods of fish scale collagen protein comprising four methods: an acid method, alkali/salt method, an enzymatic method and a hot-water, extraction method using ultrasonic wave which improves extraction of collagen from fish scale.

US20070231878 discloses a method of protein hydrolysis using enzyme and treating in warm water to extract collagen of fish scale; followed by centrifugation of the hydrolyte; taking out the supernatant of the hydrolyte rice; and drying the supernatant to become collagen powder.

US20070231878 (pg 3 para 0047) discloses extraction of collagen using acetic acid, and the method disclosed produces 90% pure collagen.

Pati et al. has reported extraction of collagen from fresh water fish scales of Rahu and Katla with higher thermal stability and ~5% yield by EDTA based dissolution [F. Pati, B. Adhikari, S. Dhara, Isolation and characterization of fish scale collagen of higher thermal stability, Bioresource Technology, 101, 3737-3742, 2010]. However, the collagen yield was found not of desired level and was limited to up to 5% of the scales by EDTA treatment.

CN 1888075 describes a method of extracting collagen from fish scale comprising of steps of defatting fish scale with mixture solution of methanol and distilled water, desalting with 0.075 mol/L concentration EDTA solution, enzymolysis with pepsin, centrifuging and spray drying to obtain crude product.

CN 1332981 discloses extraction method of collagen by stirring the scale with 14-fold warm water in a water vessel for 1 hour repeatedly.

CN 104004086 A also discloses pulsed ultrasound assisted hot water treatment where the temperature of the water is 40-80° C. and treatment time is 20-70 minutes.

Importantly, the concept of the modern development of dressing has undergone a fundamental change and now its function is not limited to cover the wound bed only but it should also promote tissue repair functions, provide habitat for the new organization to accelerate wound healing, reduce scarring and prevent bacterial contamination, and with its biodegradability, reduced the number of dressing change.

Chitosan, an amino-polysaccharide having resemblance with glycosaminoglycan, is not present in living bodies and apparently a foreign body to living organisms. A method of improving biocompatibility of chitosan by chemical modification or by blending with bioactive derivative is thus necessary. Composite biomaterial consisting of chitosan and collagen for artificial skin, artificial blood vessel, would-coating material, or adhesion preventive agent has been studied by many researchers (JP Patent Publication (Kokai) Nous. 56-133344 A (1981) and 63-59706 A (1988).

Alginate, a polysaccharide based polymer known for wound healing applications, could also be combined with chitosan, different organic acids and/or collagen to form hydrogel, superabsorbent materials for wound healing, external wound dressing and as cell delivery vehicles. In particular, hyaluronic acid, alginate, cellulose, chitosan and, to a lesser extent other polysaccharides, received attention for use for the development of several biomedical applications such as tissue engineering and controlled release of drugs and pharmaceutical proteins.

CN 1167471 describes the low cost biological composite dressing comprising of non-woven fabrics, chitosan, collagen I, and calcium alginate to be used in wound healing, has good biocompatibility, permeability, elasticity, flexibility and used as drug carriers, dosing dressing, improved for clinical use.

CN 1381274 discloses a composite biologic adhesive bandage composed of pressure-sensitive adhesive hydro-entangled cloth, hygroscopic pad, non-woven cloth, chitosan, collagen type I and medicine preparation.

Its advantages are high penetrability, elasticity, flexibility, bioactivity, biodegradability, and cost-effectiveness.

EP0200574 discloses a biologically compatible material comprising composite materials of N-succinyl chitosan and collagen for preparing wound dressing materials, vascular pro-artificial skins and hemostatic agents.

EP 1115432 relates to the fabrication of dermal scaffold and bio-artificial dermis using neutralized chitosan sponge, neutralized chitosan/collagen mixed sponge containing chitosan fabrics is mentioned and these are extremely useful for wound healing therapy.

However, there is still a need for a simpler, environmentally friendly process for extraction of collagen of high purity with minimum chemical treatment which makes the extracted collagen free from toxic chemicals and cost effective. In another aspect it is also necessary to work on advancements related to polyelectrolyte based bioactive super-absorbent having efficient wound healing property.

OBJECTS OF THE INVENTION

It is thus the primary object of the present invention to provide a process for extraction of collagen of high purity from biological wastes of different fresh water fish with minimum chemical treatment.

Another object of the present invention is to provide a cost effective and environmentally friendly process of collagen extraction by two step alkali and crushing treatment thereby minimizing the chance of collagen degradation due to chemical and/or hot water treatment.

Yet another object of the present invention is to provide collagen obtained following the above process with yield exceeding 22% total fish scale weight basis and high purity in the range of 92-95%.

A further object of the present invention is to provide polyelectrolyte based super-absorbent having efficient wound healing property and its process for manufacturing.

Yet another object of the present invention is to provide polyelectrolyte based super-absorbent having efficient wound healing property and its process for manufacture involving ionic liquids with possible interpenetrating network (IPN) based gel with significant ion-pair mediated crosslinking.

According to another aspect the present advancement is directed to the process for preparing polyelectrolyte complex including chitosan-collagen, chitosan-collagen-citrate or chitosan-collagen-alginate, chitosan-collagen-alginate-citrate or chitosan-collagen-polymaleate etc. based composite biomaterial based super-absorbent with or without antimicrobial (iodinated form of unsaturated acid/aldehyde/amine like maleic acid, hydroxy citric acid, fumaric acid, di-aldehyde etc.), antioxidant (like Kojic Acid, Curcumin), depigmenting agent (Alpha Arbutin) having efficient wound healing property and its process for manufacture.

It is still another object of the present invention is to provide for polyelectrolyte based composite biomaterials in various forms including particles, powder, flake, bead, sheet, films, fibres, spray, gel, composite based contact lenses and delivery vehicle and methods of their manufacturing.

SUMMARY OF THE INVENTION

Thus, according to the basic aspect of the present invention there is provided a process for extraction of collagen from fish scale comprising the steps of:
i) washing and softening the fish scale;
ii) subjecting the thus softened fish scale to crushing and smashing at a low temperature up to 20° C. preferably 10° C. to achieve punching and tearing of the scales;
iii) treating the crushed and smashed fish scale with acetic acid of 0.3 to 0.5 M at temperature 6 to 10° C. by stirring with shaking speed of 60-100 rpm.
iv) carrying out filtration of the acetic acid treated crushed fish scale and thus separating the solution of soluble and the residue therefrom;
v) subjecting the solution obtained to salt treatment followed by filtration to again generate solution and residue therefrom;
vi) subjecting the residue thus obtained to acetic acid treatment; followed by
vii) carrying out dialysis based wherein said step of dialysis comprises continuous dialysis process; and finally
viii) obtaining therefrom purified collagen.

Another aspect of the present invention provides a process wherein the residue in step iv) also having some collagen content is subjected to:
i) crushing and smashing;
ii) treating with acetic acid and pepsin;
iii) carrying out filtration to generate a solution of soluble and residue;
iv) recycling the solution thus obtained to carry out said steps v) to viii) and the residue to carry out said steps ii) to viii).

In yet another aspect, the present invention provides a process comprising continuous dialysis process preferably carried out involving hollow fibre membrane and dialyzer of desired molecular cut off and controlling inlet and outlet pressure at different points whereby different protein present in the solution can be separated according to their molecular weights.

A further aspect of the present invention provides a process comprising continuous dialysis process wherein said inlet pressure of the hollow fibre membrane input (collagen containing solution) is 300 to 1000 mbar and outlet pressure of the same is at 100 to 600 mbar, inlet pressure of the dialysate (water) input is maintained at 1-200 mbar below the outlet pressure of the hollow fiber membrane with continuous flow of dialysate.

In a further aspect, the present invention relates to a process wherein in the step (i) fish scales are washed with salt solution selected from NaCl or KCl, followed by softening of the scales by treating with alkali selected from NaOH or KOH, at a temperature below 15° C., preferably 4-8° C. for 24-48 h under stirring with shaking speed of 60-100 rpm.

Another aspect of the present invention relates to a process wherein the hollow membrane dialyzer has molecular cut off 3-80 kDa and the dialysis is continued till the pH of the solution is 5.5-6.5.

In another aspect, the present invention provides the process wherein the collagen obtained is with yield exceeding 22% total fish scale weight basis and high purity in the range of 92-95%.

A further aspect of the present invention relates to a process for the manufacture of a polyelectrolyte based bioactive super-absorbent material comprising:
i) providing a solution of at least one polyelectrolyte and treating with acetic acid;
ii) selectively neutralizing the polyelectrolyte solution using citrate buffer with i) selective pH controlling ionic liquid based neutralizing/buffer system with or without polyelectrolyte under continuous stirring till involving selective control of desired gelation for the formation of the cross-linked polyelectrolyte based bioactive super-absorbent including step of controlled gelation selectively for (a) slow gelation maintaining pH in the range of $pK_1$ to $pK_2$ (in the range of 3.13 to 4.7 for citrate) and (b) instantaneous gelation maintaining pH in the range of $pK_2$ or above (in the range of 4.76 or higher up to 12 especially for citrate buffer).

Yet another aspect of the present invention relates to a process for the manufacture of a polyelectrolyte based bioactive super-absorbent material wherein said ionic liquid include unsaturated acids including organic acids containing more than one pKa values selected from citric, hydroxy citric acid, oxalic, fumaric, ascorbic, lactic, pyruvic, succinic, lipid, maleic, malonic, glucaric, succinic, adipic, pamelic, subaric acid, Kojic Acid, Alpha Arbutin having several pKa values and with varied pH for desired selective used in the form of ionic liquid for neutralizing and forming ion-pairs mediated cross-linked material selected from hydrogel, film, particles, beads, fibers, powder, flakes, sponge, sheet, particle suspension spray, in-situ gelation during spraying;
said polyelectrolytes including polymers preferably are selected from polyvinyl alcohol, silk alginate, chitosan, polyfumaric acid, poly maleic acid etc and other synthetic biopolymers and semi-synthetic polymers.

A further aspect of the present invention relates to a process for the manufacture of a polyelectrolyte based bioactive super-absorbent material wherein for forming interpenetrating network (IPN) based gel with significant ion-pair mediated crosslinking both the neutralizing solutions/buffer contains polyelectrolyte, said ion-pair providing a highly interconnected porous template facilitating anyone or more of protein adsorption, growth factor adhesion and cell adhesion.

Another aspect of the present invention provides a process for the manufacture of a polyelectrolyte based bioactive super-absorbent material wherein said cross linked polyelectrolyte based bioactive super-absorbent is obtained including covalent or ionic cross linking preferably including in situ iodination during crosslinking for generating iodinated cross linked polymer dressing system.

In yet another aspect of the present invention is related to a process for the manufacture of a chitosan based bioactive super-absorbent material comprising:
i) providing a solution of at least one of (a) chitosan and (b) a mix of chitosan-collagen in the weight ratio of 20:0.25-10 wt % and treating with acetic acid;
ii) treating the solution of i) above with polycarboxylic acid based system under continuous stirring till involving selective control of desired gelation for the formation of the chitosan based bioactive super-absorbent including step of controlled gelation selectively for (a) slow gelation maintaining pH in the range of $pK_1$ to $pK_2$ (3.13 to 4.7 for citrate) and (b) instantaneous gelation maintaining pH within the range of $pK_2$ or above (in the range of 4.76 or higher up to 12 for citrate).

Another aspect of the present invention relates to a process for the manufacture of a chitosan based bioactive super-absorbent material comprising:
i) providing a mix of chitosan-collagen in the weight ratio of 20:0.25-10 wt % by adding 0.1 to 1 M acetic acid to the final concentration of the solution 5 to 10 wt % depending upon the molecular weight of chitosan used;
ii) neutralizing the solution by addition of citrate buffer in the range of 1 to 10 wt % under continuous stirring to thereby reduce the charge density of chitosan gradually until the solution was completely neutralized.

In a further aspect of the present invention is provided for a process for the manufacture of a chitosan based bioactive super-absorbent material for producing selectively anyone or more of chitosan-collagen particles, powder, flakes and beads comprising:
(i) carrying out said neutralization of chitosan-collagen solution by mixing with citrate buffer under continuous stirring maintaining pH range of citrate buffer more than 3.13 preferably at 7.4;
(ii) casting the neutralized solution;
(iii) storing the thus cast solution in freezer at −20° C. to −80° C. preferably at −80° C. for 10 to 24 hrs preferably at 12 hrs; followed by;
(iv) lyophillization at <−30° under vacuum $1\times10^{-1}$-$5\times10^{-2}$ mbar or below until the beads or freezing solution has dried substantially or completely;
(v) crushing the dried mix to obtain therefrom selectively anyone or more of bioactive super-absorbent chitosan-collagen particles, powder, flakes and beads.

A further aspect of the present invention relates to a process for the manufacture of a chitosan based bioactive super-absorbent material for producing selectively anyone or more of chitosan-collagen particles, powder, flakes and beads comprising:
(i) carrying out said neutralization of chitosan-collagen solution by drop wise addition of citrate buffer under continuous stirring maintaining pH range of citrate buffer in the range of 4.76-10 preferably at 7.4 to thereby obtain neutralized beads;

(ii) storing the thus neutralize beads in freezer at −20° C. to −80° C. preferably at −80° C. for 10 to 24 hrs preferably at 12 hrs; followed by;
(iv) lyophillization at <−30° under vacuum $1\times10^{-1}$-$5\times10^{-2}$ mbar or below until the beads or freezing solution has dried substantially or completely optionally involving temperatures of 40-80° C.
(v) obtaining from the dried beads selectively anyone or more of bioactive super-absorbent chitosan-collagen particles, powder, flakes and beads.

In another aspect, the present invention relates to a process for the manufacture of a chitosan based bioactive super-absorbent material wherein said dried beads directly or following crushing, sieved in meshes of varied mesh sizes to thereby obtain selectively anyone or more of bioactive super-absorbent chitosan-collagen particles, powder, flakes and beads.

A further aspect of the present invention relates to a process for the manufacture of a chitosan based bioactive super-absorbent material for producing chitosan-collagen sheets comprising:
i) providing a solution of at least one of (a) chitosan and (b) a mix of chitosan-collagen in the weight ratio of 20:0.25-10 wt %;
ii) neutralizing the solution by mixing said chitosan or chitosan-collagen solution with citrate buffer under continuous stirring till the solution was completely neutralized to different extent;
(iii) casting the neutralized solution;
(iv) storing the thus cast solution in freezer at −20° C. to −80° C. preferably at −80° C. for 10 to 24 hrs preferably at 12 hrs; followed by;
(v) providing neutralized collagen solution;
(vi) pouring the neutralized collagen solution on top of the said frozen chitosan solution or said frozen chitosan-collagen to provide a collagen layer followed by
(vii) freezing 20° C. to −80° C. and preferably at −80° C. for 10 to 24 hrs preferably at 12 hrs and lyophillization at <−30° C. under vacuum $1\times10^{-1}$-$5\times10^{-2}$ mbar or below into sponge;
(viii) pressing the sponge to obtain sheets therefrom.

In another aspect, the present invention relates to a process wherein the said step of casting was carried out in a tray preferably a Teflon coated tray and stored in freezer at −20° C. for 12 hrs; and opposite to the collagen layer of said sheet there is provided a non-adhesive mesh either by pressing or involving cellulose based adhesive to provide support to the sheet, form a non-sticky barrier and retain the shape of the sheet.

In a further aspect of the present invention is related to a process for the manufacture of a chitosan based bioactive super-absorbent material for producing chitosan-collagen sheets comprising:
i) providing neutralized chitosan solution;
ii) mixing the neutralized chitosan solution with alginate-citrate buffer to form gel;
(iii) casting the gel in tray;
(iv) storing the thus cast solution in freezer at −20° C. to −80° C. preferably at −80° C. for 10 to 24 hrs preferably at 12 hrs; followed by;
(iv) providing neutralized collagen solution;
(v) pouring the neutralized collagen solution on top of the said frozen gel to provide a collagen layer; followed by
(vi) lyophillization at <−30° C. under vacuum $1\times10^{-1}$-$5\times10^{-2}$ mbar or below into sponge.

In a still further aspect, the present invention relates to a process for the manufacture of a chitosan based bioactive super-absorbent material for producing chitosan-collagen films comprising:
(i) carrying out said neutralization to different extent of chitosan-collagen solution with citrate buffer under continuous stirring maintaining pH range of citrate buffer in the range of 3.13 to 4.76 maintaining pH of neutralized solution in the range of 5-7;
(ii) casting the neutralized solution and drying under sterilized condition preferably under air flow until solution dried completely to form film.

In another aspect, the present invention relates to a process for the manufacture of a chitosan based bioactive super-absorbent material for producing chitosan-collagen fibers comprising:
preparing said chitosan-collagen solution by adding 0.1-1.0 M acetic acid using 0.1-1.0 M acetic acid to the solution of 0.5-5 wt %;
filtering the solution and wet spinning the filtrate in polycarboxylic acid bath at varied pH with pKa values higher than at least two carboxylated group ionization (above $pKa_2$) to thereby obtain the chitosan-collagen fibers.

Yet another aspect of the present invention relates to a process wherein the filtrate was wet spun in a citric acid bath with pH between 4.76 and 10 preferably at 7.4; followed by washing the fibers and drying.

In a further aspect of the present invention is related to a polyelectrolyte based bioactive super-absorbent material comprising: polyelectrolyte based bioactive super-absorbent which is ionotropically crosslinked/neutralized involving polyvalent carboxylic acids.

In yet another aspect, the present invention relates to a polyelectrolyte based bioactive super-absorbent material comprising collagen-biopolymer which is ionotropically crosslinked/neutralized involving polyvalent carboxylic acids.

In a further aspect, the present invention relates to a polyelectrolyte based bioactive super-absorbent material comprising variable pH based neutralized and formed ion pair mediated cross linked products including selectively anyone or more of dressing system including iodinated crosslinked polymer as antimicrobial agent, in combination with any antibacterial, anti-fungal, anti-inflammatory and antioxidant along with Kojic Acid and Alpha Arbutin as skin plumper and melanin reducer in the form of beads, sheet, Film and fiber blanket.

Yet another aspect of the present invention provides a polyelectrolyte based bioactive super-absorbent material comprising fish scale collagen based wound healing/dressing including partial, full thickness, diabetic, chronic, traumatic, ulcer, exudating wounds, bone cartilage healing, cell/drug/different bioactive molecules cytokines, chemokines delivery vehicles, scaffold for tissue engineering, 3D cell expansion media, collagen delivery in dry eye, collagen based health drink and food, intra ocular lens, contact lens, oral patch, ingredients for capsules, mineral delivery, moisturizer, ointments, facial creams.

A further aspect of the present invention provides a polyelectrolyte based bioactive super-absorbent material comprising fish scale collagen cross linked with other polyelectrolyte biopolymers preferably selected from chitosan and alginate.

A still further aspect of the present invention relates to a polyelectrolyte based bioactive super-absorbent material and/or in combination of live cells in other healing agents which is utilized in the form of spray or injectable in-situ gelation on wound site.

Another aspect of the present invention provides a polyelectrolyte based bioactive super-absorbent material including collagen based substrates and/or collagen based IPN selectively in the form of coatings on cell culture vessels, beads, micro-beads, sponge, sheets, fibrous 2D/3D scaffold useful for 2D/3D cell culture, cell expansion and cell delivery vehicle delivery for cell biology assay, therapeutics and preparation of conditioning medium including in any stem/primary/malignant cells alone or in any combinations thereof.

In another aspect the present invention provides a polyelectrolyte based bioactive super-absorbent material wherein as coatings on cell culture vessels the same are obtained in various shapes and designs matching the cell culture vessel shape and dimensions.

Yet another aspect of the present invention relates to a cell culture system comprising subjects including polyelectrolyte based bioactive super-absorbent material comprising ionotropically crosslinked/neutralized involving polyvalent carboxylic acids as collagen based substrates and/or collagen based IPN.

A still further aspect of the present invention relates to a cell culture system comprising cell culture vessels for static/dynamic culturing selectively (i) for cells in 2D having said collagen based substrates and/or collagen based IPN coating and (ii) for cells in 3D having said collagen based substrates and/or collagen based IPN in the form of beads, microbeads, sponge, sheets, fibrous 3D scaffold.

In yet another aspect, the present invention provides a cell culture system comprising said coated cell culture vessels obtained selectively of of thermoformed polymer sheet of thickness in the range of 50 to 2000 micron (μm) and of any thermoplastic or thermosetting polymers including polystyrene of various design template with said coating enablement.

A further aspect of the present invention provides a cell culture system including which is capable of mechanical device for cyclic deformation involving any external mechanical device induced mechanotransduction of cells differentiation assembly and/or allowing direct imaging including various design of the cell culture dish/vessel including open, partially closed, closed, semipermeable membrane enclosure suitable for static and/or dynamic conditions. In a still further aspect the present invention provides a cell culture system which is capable of mimicking the in vivo situation in dynamic condition including as substitute of in vivo animal model for assessments of cytotoxicity, drugs responses, and other related studies.

DETAILED DESCRIPTION OF THE INVENTION

As discussed herein before the present advancement provides a simple process for collagen extraction from fish scales without using toxic chemicals. Moreover the present advancement also provides a process for manufacture of collagen-chitosan composite biomaterial in various forms which is useful in would dressing and wound healing.

The process of the present advancement replaces a number of steps of the existing processes by two steps comprising alkali treatment followed by crushing/smashing making the process simple, fast, economic, and minimizes the chances of collagen degradation as a result of previously reported chemical and/or hot water treatments.

Advantageously, according to a preferred aspect the advancement involves dialysis of the collagen containing solution with hollow fiber membrane which would effectively replace the batch type membrane based osmosis by enabling a continuous hollow fiber membrane based reverse osmosis. Thus for protein purification, the reverse osmosis based hollow fiber dialysis membrane is utilized via continuous flow based dialysis process where collagen is separated from solution containing collagen, NaCl, Acetic acid and other minor impurities of small molecules and ions by dialysate (water in this process).

Importantly, using dialyzer of different molecular cut off and controlling the inlet and outlet pressure of the dialyzer at different points, the different proteins present in the solution can be separated according to their molecular weight. The process as a whole (sequential NaCl, NaOH treatment followed by smashing/crushing and treatment of the smashed/crushed scale by acetic acid and pepsin-acetic acid alternatively) accelerated the dissolution of the collagen molecules from scale. The complete dissolution of the scale can be achieved in 15-18 weeks. After the first three dissolution steps, the collagen yield increased significantly.

Collagen is an important protein containing 'RGD' moiety for adhesion of cells via surface integrin receptors and can also be utilized for cross-linking mediated entrapment and slow release via ion exchange for different health care applications. Collagen has isoelectric point (IEP=5.1) like any other proteins and acts as a charged molecule at pH away from IEP.

Chitosan, being a polycataionic amino polysaccharide, has structural resemblance with GAGs having wound healing efficacy, mucoadhesivity, biocompatibility and non-toxicity. Chitosan bio-polymer has various applications in the field of hydrogels formation, tissue engineering, wound dressings and drug delivery systems. Under dissolved state in organic acid like acetic acid, chitosan becomes positively charged through protonation in the amine functional group (pKa~6.5).

Several organic acids (e.g. citric, oxalic, fumaric, lipid, maleic, malic, glucaric, ascorbic, lactic, pyruvic, succinic, subaric, hydroxy citric acid, Kojic Acid, Alpha Arbutin etc.) containing polycarboxylic acids are used in formulating ionic liquids and are degradable via metabolic pathway in vivo. These acids also have antioxidant properties which are effective in scanvanging reactive oxygen species. Different polyelectrolytes (like alginate, chitosan, polyfumaric acid, poly maleic acid) could be neutralized by opposite charge ions at suitable pH range that can be detected via potentiometric or conductometric titration forming ionotropic gelation, neutralization, complexation. If both the neutralizing solutions/buffer contains polyelectrolyte, they also form interpenetrating network (IPN) based gel with significant ion-pair mediated crosslinking. These ion-pair network containing highly interconnected porous template acts as zwitter ions for ultra low fouling activity preventing non-specific protein adsorption and facilitates necessary protein, growth factor and cell adhesion. Ion-pair mediated crosslinked gel is dried under super critical temperature for formation of superabsorbent and the ion-pairs could promote absorption of very high weight percentage of polar solvent medium like water. In fact animal extracellular matrices are also naturally occurring interpenetrating gel network. IPNs, semi- or full-IPN may also have different types of physical, ionic, covalent interactions depending on nature of the material used.

Different organic acids including mono, di, tri and poly-carboxylic acids (like Kojic Acid, Alpha Arbutin, ascorbic, lactic, pyruvic, succinic, citric, hydroxy citric acid, oxalic, polymaleic, polyfumaric, tarmaric, fumaric, maleic, malic, subaric etc.) have several pKa values. These molecules with varied pH could be efficiently used in the form of ionic liquid for neutralizing and forming ion-pairs mediated cross-linked hydrogel, film, particles, beads, fibers, powder, flakes, sponge, sheet etc. In case of citric acid, citrate has $pK_a$ ($pK_{a1}$=3.13, $pK_{a2}$=4.76, $pK_{a3}$=6.39) values which vary within 3.13 to 6.39. The citric acid solution with pH value within range of 3.13 to 4.76 could be used only for neutralization, whereas pH values ranging from 4.76 to 6.39 and higher than that could be used for neutralization and citrate mediated crosslinking. The hydrogels can also be formed by using combination of two or more electrolytes, molecules types and/or in combination with other types of cross linking like covalent, hydrogen bonding etc.

The details of the invention, its objects and advantages are explained hereunder in greater detail in relation to the following non-limiting accompanying figures and examples.

BRIEF DESCRIPTION OF ACCOMPANYING FIGURES

Figure 2:
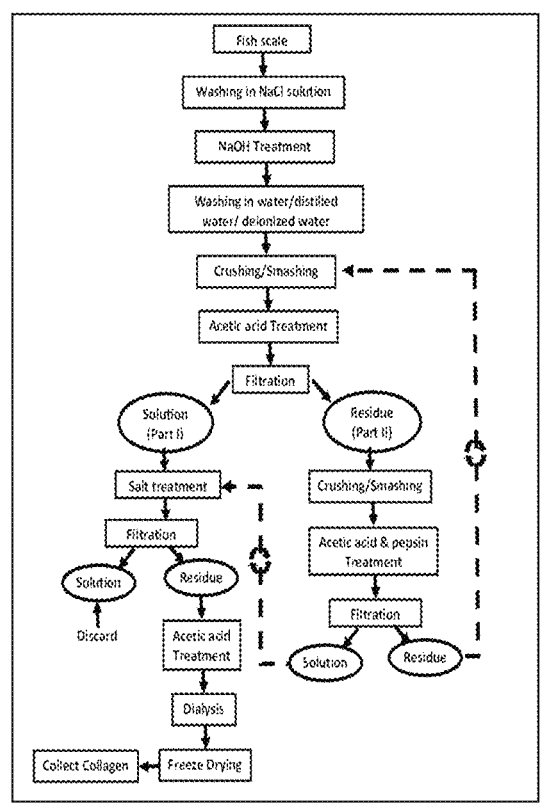
Figure 3:
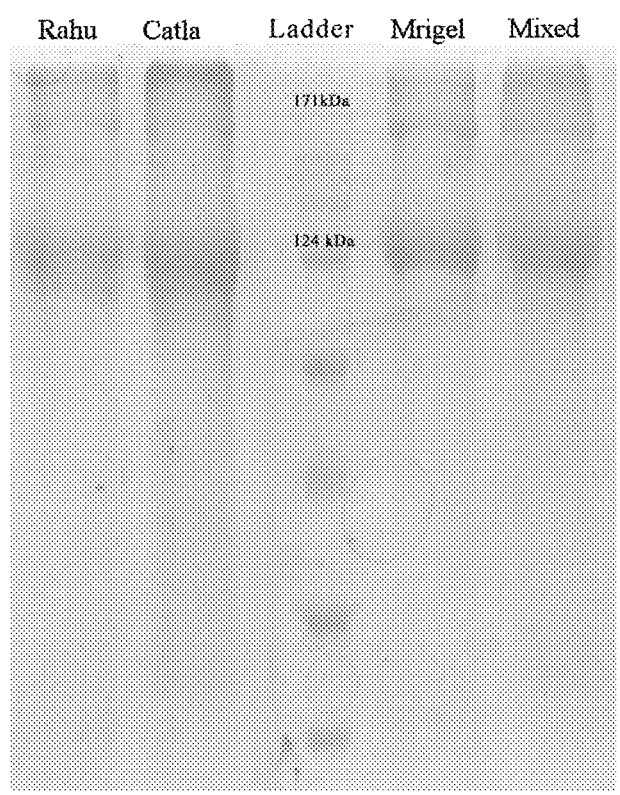
Figure 4:
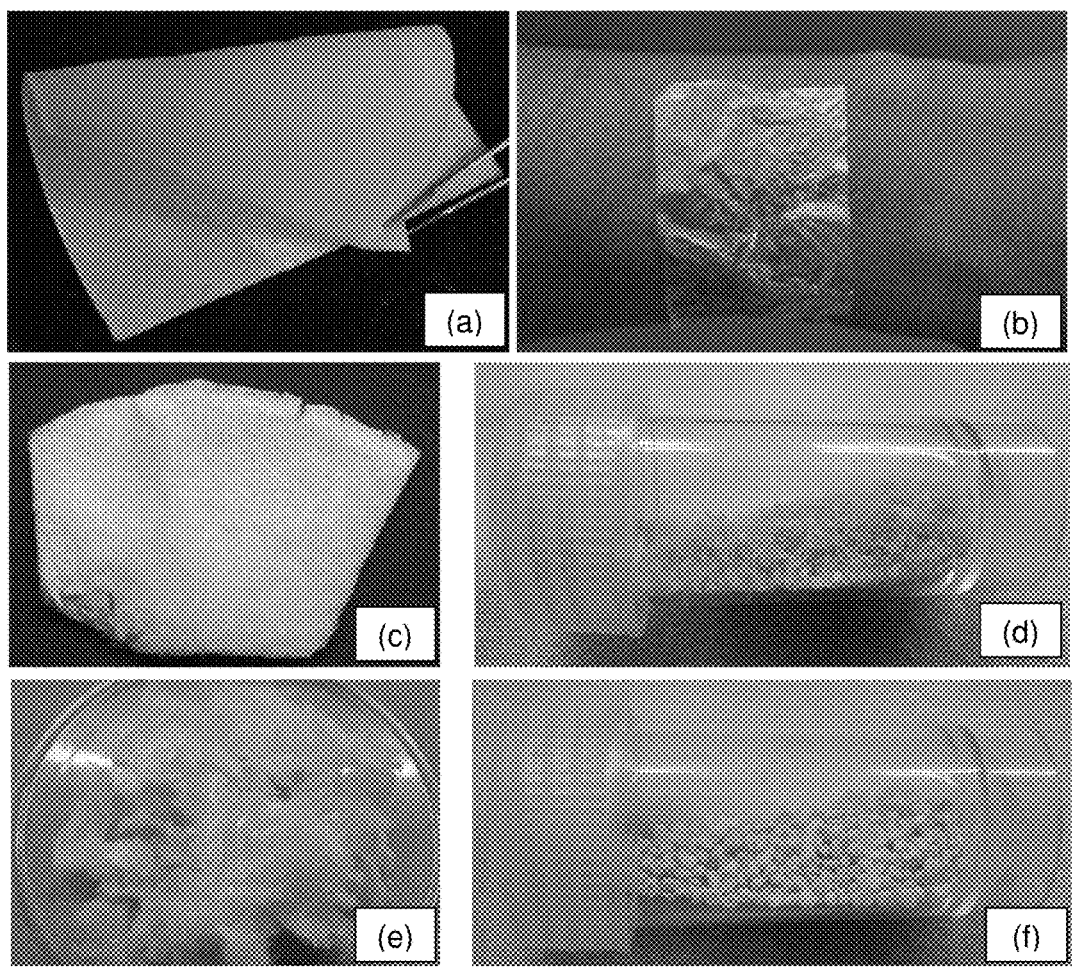

FIG. 1: illustrates optical images of collagen sponge obtained after lyophilisation;

FIG. 2: illustrates the flow diagram of collagen extraction from fresh water fish scale;

FIG. 3: illustrates electrophoretic patterns of Type I collagen obtained from fish scale of Rahu, Catla, Mrigel and mixed species;

FIG. 4: illustrates collagen based different forms; (a) sheet (b) film (c) sponge (d) particles (e) fibers and (f) beads;

Fresh water fish origin of Indian subcontinent, East and South-east Asia (such as Golden Carp, Silver Carp, Grass carp, Labeo Bata, Lata, Catla, Rahu, Mrigel, Shol, Talapia, Nilontika, Hilsa, Bhetki, Balichura, Barali, Bata/Bangna, Bele, Rupchand, Cypinus, Chital, Foli/Chitol, Chuna, Common carp ((*Channa gachua, Channa orientalis*), Gozar (*Channa marulius*), Ilish (*Tenualosa ilisha*), Kalibaus, Nilotica (*Oreochromis*), Japanese Pnuti, Koi, Putitor mohashoul, Mohashoul, Shorpunti, Tapse, Mourala etc.) including fish scale are good source of collagen.

Scales and other biological wastes of Fresh water fish of individual species (Rahu, Katla, Mrigel) and the mix scales of the above mentioned species (henceforth will be referred as mixed species) were collected from fish market of Contai, East Midnapur, West Bengal, India.

Example 1: Extraction of Collagen Type I from Fish Scale

Fresh water fish scale of 1000 g was taken and washed with water thoroughly. It was again washed with 0.2-0.5M NaCl solution. After washing, the fish scale is kept in a container and soaked in 0.2-1.0 M preferably 0.5M NaOH solution for 24 to 48 h in a BOD incubator shaker with a shaking speed of 60-100 r.p.m and at temperature below 10° C.; preferably at 4° C.

After soaking, alkali treated scale was washed with distilled water and smashed/crushed in a grinder/crusher while maintaining the temperature below 20° C. by adding ice/ice water intermittently.

The smashed/crushed scale was kept in a container along with 0.5 M acetic acid solution (acid solution:scale=10-20:1 ratio by weight) for 7 days in a BOD incubator shaker at <10° C. and 60-100 r.p.m. After 7 days, the solution was filtered with nylon/cotton net of porosity 300-1000 µm to recover the scale. The filtered solution (Part I) was collected in a container. The residue (Part II) is also collected in another container.

In the solution (Part I), NaCl was added pinch by pinch and was gently shaken in a magnetic stirrer at r.p.m.<150. The dissolved collagen precipitated out form the solution continuously. Salt addition process was continued until the concentration of NaCl in the solution became 0.9 M. Then the precipitate was separated from the solution by a specially designed filter system where filtration was carried out in a single step using cloth filter (in the range of 50-500 µm). After filtration, the precipitate was collected and the filtrate was discarded.

The collected precipitate was re-dissolved in 0.3-0.5M acetic acid by gentle stirring. The dissolved solution was dialyzed in a hollow fiber membrane dialyzer (molecular cut off 3-80 kDa). The inlet pressure of the solution was kept at 300-1000 mbar and outlet pressure was at 100-600 mbar. The inlet pressure of water was kept at 0-200 mbar below the outlet pressure of the solution. The dialysis was continued until the pH of the solution reached in the range of 5.5 to 6.5. The solution obtained after dialysis was frozen at −20° C. for 12 h followed by lyophilizing at <−30° C. for 24 to 48 h under vacuum. After freeze drying the purified collagen sponge was collected (FIG. 1).

The collected residue (Part II) was smashed/crushed in ice-water mixture in a grinder/crusher and the ground/crushed scale was kept in a container. 0.5 M acetic acid (acid solution:scale=10-20:1 ratio by weight) and 0.1% pepsin were added in the bottle. The bottle containing scale and chemicals was kept under shaking condition for 3 days in a BOD incubator shaker at <10° C. at 60-100 r.p.m. After 3 days, solution and residue were collected separately. Same treatment, as given to part I solution, was applied to this solution and the same procedure was followed to obtain collagen from this solution. The residue was recycled and again smashed/crushed followed by acetic acid treatment and filtration to obtain part I and part II, as described above. The process of extraction collagen from fish scale is shown schematically in FIG. 2.

Washing in NaCl removes the odour and colour/pigment from the scale and therefore, high purity collagen isolation is possible by minimizing the filtration which is significantly time consuming. The removal of pigment subsequently helps to reuse the hollow fiber membrane for more number of times.

NaOH treatment makes the scale softer with significant swelling characteristics to facilitate grinding/crushing without significant increase in the temperature and protein degradation.

This step of grinding/crushing promotes exposure of collagen into acidic environment during acetic acid treatment, which further facilitates easy dissolution of collagen without demineralization of scale.

The hollow fiber membrane was used for dialysis and purification which could be advantageously reused several times (4-10 times) and collagen production rate increased significantly.

Thus, in this method, the minerals were not attempted to be demineralized by EDTA treatment as demineralization by chelating is time consuming and costly affair, which also eliminates the possibility of presence of remnant EDTA (a chelating agent for $Ca^{+2}$, $Fe^{+2}$, $Fe^{+3}$ causing demineralization) in the isolated collagen.

Example 2: Characterization of the Extracted Collagen Obtained from Ex 1 i) SDS-PAGE:

Electrophoretic patterns of Type I collagen from fish scale of Rahu, Catla, Mrigel and mixed species is shown in FIG. 3. In all the cases (i.e. Rahu, Catla, Mrigel and mix sources) the mobility of O-chains was obtained as expected, based on the molecular weight markers.

The estimated molecular weight for a chain of these collagens, using globular proteins as standards was approximately 120-150 kDa. As in type I collagen from calf skin which was compared with the isolated collagens comprised of at least two different α-chains (α1 and α2) with different mobility, which indicated that the collagens from these two species are of type I collagen.

ii) FTIR Analysis:

In the FTIR spectra of fish scale collagen of mixed species, the amide I band found is in the range from 1600 cm$^{-1}$ to 1700 cm$^{-1}$. This is mainly associated with stretching vibrations of the carbonyl groups (C=O bond) along the polypeptide backbone, which is a sensitive marker of the peptide secondary structure. The ratio of absorption intensity between 1240 cm$^{-1}$ (amide III) and 1463 cm$^{-1}$ (amide II) band is approximately equal to 1.0, which confirms the triple helical structure of collagen.

iii) Amino Acid Analysis by HPLC:

The amino acid composition of the collagen isolated from mixed species of fresh water fish scale was expressed as amino acid residues per 1000 total amino acid residues and is shown in Table 1. As collagen is triple helical in nature with characteristic amino acid repeat, (Gly-Pro-Hyp), glycine (Gly) was the most abundant with the amount of 340 of the total amino acid present in collagen extracted from mixed species. The total amount of imino acids per 1000 total amino acid residues, proline (Pro) and hydroxyproline (Hyp), are 120 and 80, respectively, which is likely to have effect on the stability of the collagen fibers and influences the denaturation temperature as well. Absence of cysteine in collagen emphasizes presence of type I collagen. The hydroxyproline content in the collagen isolated from scale of Katla, Rahu, Bata, Mrigel etc. (fresh water fish origin) had marginal variation which was significantly higher than the marine source and thus significantly higher thermal stability.

TABLE 1

Amino acid composition of ASC from scale of Mixed species (expressed as residues per 1000 total amino acid residues)

| Amino acid | Residues/1000 residues |
|---|---|
| Aspartic acid/Asparagine | 47 |
| Cysteine | 0 |
| Glycine | 340 |
| Hydroxyproline | 80 |
| Glutamic acid/Glutamine | 77 |
| Alanine | 115 |
| Proline | 120 |
| Lysine | 26 |
| Valine | 22 |
| Methionine | 14 |
| Isoleucine | 10 |
| Leucine | 23 |
| Serine | 35 |
| Threonine | 21 |
| Tyrosine | 3 |
| Phenylalanine | 13 |
| Tryptophan | 0 |
| Histidine | 4 |
| Arginine | 50 |

Example 3: Yield Percentage of Different Fish Scales

Using this procedure, the mixture of scale from different spices yielded collagen up to 22% which is substantially higher than the most of the reported values. The collagen yield was up to 5% of the scales by EDTA treatment and acetic acid dissolution as discussed in the F. Pati et al without crushing of the scales.

Example 4: Collagen Based Wound Dressing

Collagen extracted by the Example 1 is used to prepare different forms of products for wound dressing by combining with a polysaccharide such as chitosan, alginate or their combination followed by citrate buffer neutralization. The basic steps comprise:

i) Chitosan-collagen solution at different weight ratio (20: 0.25-10 wt % on total weight basis) was prepared individually or as a mix by adding 0.1-1 M acetic acid to the final concentration of the solution 0.5-5 wt % depending on the molecular weight of chitosan used.

ii) The solution was further neutralized to a different extent by drop wise addition of 5 wt % citrate buffer (in the range of 1-10 wt %) at varied pH but higher than 3.13 (preferably at pH 7.4) under continuous stirring by mechanical/magnetic stirrer (200-300 r.p.m.) to reduce the charge density of chitosan gradually.

iii) When pH of the solution reached to 7.0 the appearance became white and the solution was completely neutralized.

iv) The neutralized solution was then cast in a tray (preferably in Teflon coated tray) and stored in freezer at −20° C. for 12 h followed by lyophilisation at <−30° C. under vacuum of $1 \times 10^{-1}$-$5 \times 10^{-2}$ mbar or below until the freeze solution dried substantially.

v) The dried mix was crushed and sieved by nylon/cotton mesh of varied mesh sizes.

vi) The different forms (particles, powder, flake, bead etc.) obtained after sieving were stored in an air tight bag under sterilized condition at room temperature or below for final applications.

These downstream products like collagen based sheet, film, sponge, particles, fibres and beads are shown in FIG. 4.

Example 5a: Preparation of Chitosan-Collagen Powder, Particles, Flakes and Beads To form beads, citrate buffer (in the range of 1-10 wt %) at pH in the range of 4.76 to 10 (preferable at pH 7.4) is added to the solution of Example 4 following under continuous stirring by mechanical means (200-500 r.p.m.) to reduce the charge density of chitosan and form beads. When pH of the solution was closed to 7.0 the appearance of neutralized beads turned into white and looked like precipitate. The beads were collected, washed and dried to a different extent and by different means. The neutralized beads were stored in freezer at −20° C. for 12 h followed by lyophilisation at <−30° C. under vacuum of $1 \times 10^{-1}$-$5 \times 10^{-2}$ mbar or below until the beads dried substantially or completely. The drying of beads was also attempted under vacuum ($1\times10^{-1}$-$5\times10^{-2}$ mbar or below) or in a temperature controlled oven (at 40-80° C.). Finally the beads were either crushed followed by sieving or directly sieving in nylon/cotton mesh of varied mesh sizes and depending upon the mesh size different forms like powder, particles, flakes and beads were obtained.

Example 5b: Preparation of Chitosan-Collagen Sheet

The differentially neutralized chitosan/chitosan-collagen solution obtained in Example 4 was then cast in a tray (preferably in Teflon coated tray) and stored in freezer at −20° C. for 12 h.

2.5 wt % collagen solution was prepared separately by adding collagen in 0.3 M acetic acid solution (250 mg collagen in 10 ml acetic acid solution). This solution was neutralized by adjusting the pH with 5 wt % citrate buffer.

The collagen/neutralized collagen solution was poured on the top of the frozen mix followed by similar freezing and lyophilisation (at <−30° C. under vacuum of $1\times10^{-1}$-$5\times10^{-2}$ mbar or below) into sponge. The sponge was pressed into different extent to form sheet of required thickness. Opposite to collagen layer of the sheet, a non-adhesive mesh (nylon or any other similar materials) was fixed either by pressing or by using cellulose based bio-adhesive in order to provide support to the sheet, form a non-sticky barrier and retain the shape of the sheet Optionally, 1-5 wt % alginate solution was prepared with distilled water by shaking in any mechanical means. 5 wt % citrate buffer was added (ratio of alginate solution to citrate buffer was 5-10:1 by volume) drop wise to the solution by continuous mechanical/magnetic stirring (100-300 rpm) to increase charge density of the solution.

The separately prepared neutralized chitosan (by the method of Example 4) solution was mixed with alginate-citrate buffer to form gel. The gel was cast in a tray (preferably in Teflon coated tray) and subsequently frozen in a freezer at −20° C. for 12 h. Then the neutralized collagen solution was poured on the top of frozen mix in the tray and lyophilized at <−30° C. under vacuum of $1\times10^{-1}$-$5\times10^{-2}$ mbar or below. Sponge was formed after complete lyophilization.

The sponge was pressed into different extent to form sheet of required thickness. Opposite to collagen layer of the sheet, a non-adhesive mesh (nylon or any other similar materials) was fixed either by pressing or by using cellulose based bio-adhesive in order to provide support to the sheet, form a non-sticky barrier and retain the shape of the sheet. The sheet was stored in an air tight bag under sterilized condition at room temperature or below for further applications.

Example 5c: Preparation of Chitosan-Collagen Film

The neutralized solution of Example 4 was cast in a tray (preferably in metallic (like stainless steel)/glass/polymer based tray) and dried under sterilized condition preferably under air flow until the solution dried completely to form the film. The film was carefully removed and stored under sterilized sealed bag at room temperature or below for further applications.

Example 5d: Preparation of Chitosan-Collagen Fiber

Chitosan-collagen solution obtained from Step 1 of Example 4 was filtered and the filtrate was wet spun in polycarboxylic acid bath at varied pH with pKa values higher than at least two carboxylated group ionization (above $pKa_2$). The filtrate was also wet spun in a citric acid bath with pH between 4.76 and 10 preferably at 7.4. The fibers were washed, dried and kept in air sealed bag to store at below 30° C. preferably at 15° C. under sterilized condition for final applications.

Example 5e: Preparation of Chitosan-Collagen Spray

The chitosan-collagen powder prepared in 5a was suspended in aqueous/dilute acetic acid medium and could be sprayed on the wound bed prior to covering by occlusive dressing. The collagen-citrate based solution/suspension could also be sprays on the assaulted area.

Example 5f: Preparation of Chitosan-Collagen Spray-Gel

Chitosan-collagen mix (20:1-10 wt % on total weight basis) solution using 0.2 mol % acetic acid with pH below 6 along with citric acid (1-10 wt %) solution at pH above 5 were promoted for in-situ gelation during spraying using a special spraying device which facilitated mixing of both the solution into gel at the specific site of interest.

Example 5g: Preparation of Collagen Based Transparent Film, Curved Contact Lenses, Delivery Vehicles Blending collagen with other polymer like Polyvinyl alcohol, silk or chitosan (20:1-10 wt % on total weight basis) followed by co-valent/ionotropic crosslinking. Covalent or ionic crosslinking using unsaturated acid/aldehyde/amine etc. also favours in situ iodination during crosslinking using iodine as blend. This iodinated crosslinked polymer dressing system is efficient in antimicrobial activity due to slow release of iodine into the wound site.

Example 6: Characterization of Chitosan-Collagen Based Wound Dressing

1) Swelling Study:

Collagen, chitosan-collagen, and chitosan-alginate-collagen samples (in example 5a to 5g) showed a steady state of swelling in 48 h of soaking period without any disintegration or dissolution in the medium and preserved their physical integrity. The sponge and sheet samples showed a rapid swelling in first 10-24 h because of rapid diffusion of water molecules. Then it gradually attained equilibrium in about 36 h and maintained equilibrium swelling state. The sheet showed higher swelling than the other forms and after 24 h it reached to ~6000%.

ii) Degradation Study:

The enzymatic degradation of raw collagen and collagen based different samples (in example 5a to 5g) were investigated by monitoring the residual mass percent as a function of exposure time to collagenase solution. The collagen samples degraded rapidly compared to the chitosan-collagen samples. Within 24 h. the residual mass reduced to 18.4% of the initial mass for sponge/sheet (example 5b).

vi) In Vivo Animal Study (Full-Thickness Cutaneous Wound Models)

Thirty-six rats (male wistar weighing~220 g) divided into two groups were studied for wound healing under animal ethical clearance using standard protocol. A full-thickness square defect (2 cm×2 cm) was created in the upper back area of each rat and then implanted with or without a chitosan-collagen film/sheet. Wounds were wrapped with dressing for protection. Wound closure was measured every other day after wounding. Animals were euthanized after 14 days and tissues were harvested for analysis. All the tissue samples were cut into a full-thickness manner from the wounded sites, and then were used for histological analyses. Photographic images were also captured to understand the healing process. The entire studies were carried out under ethical clearance.

Measurement of Wound Healing:

The wound healing process after treatment with a collagen-chitosan sheet and film and its comparison with the healing process of the control is shown in FIG. 7. During the first day post-operation, the collagen-chitosan sheet and film efficiently absorbed wound exudates and tightly attached to the wound surface.

After 5 days of post-operation, scabs were observed in both groups which after 10 days post-operation, were falling off the wounds, and the wounds were mostly filled with restored skin. It is notable that the wounds of the collagen-chitosan sheet and film group were greatly reduced in size as compared to the control which is more evident after 15 days. Complete wound closure was observed in collagen-chitosan sheet treated group after 18 days. The restored skin treated with a collagen-chitosan sheet and film was similar to normal skin, while an elongated scar was still observed in the skin after healing of a control group due to excessive contraction.

The defects treated with collagen-chitosan sheet demonstrated superior healing and the skin defect was reconstructed with a good cosmetic outcome. The wound area decreased at an accelerated rate for the wounds treated with collagen-chitosan sheet and collagen-chitosan film at the end of $14^{th}$ day compared to the control. The difference between the control group and the collagen-chitosan sheet/film group showed significant healing compared to the control after 14 days of treatment ($p<0.05$). From this animal study, the positive role of collagen and citric acid in accelerating wound healing is evident.

vii) Tensile Strength of Regenerated Skin:

Assessment of regenerated skin tissues was done by measuring the mechanical properties of the regenerated tissues. Analysis of the all biomechanical parameters (mainly ultimate tensile strength and young's modulus) demonstrates that biomechanical property of collagen-chitosan sheet and collagen-chitosan film treated group was better compared to the control group.

viii) Histological and Immunofluorescence Studies

Histological analyses were performed to assess the regenerated tissues guided by collagen-chitosan based samples (in example 5a to 5g) in rats. H&E staining of wound sections after 14 days post-surgery revealed distinct differences in maturity of the epidermis/dermis and quality of granulation tissue between collagen-chitosan sheet/film-group and the control group. Both collagen-chitosan sheet and collagen-chitosan film-group demonstrated accelerated maturation and a well formed epidermis with compact orthokeratosis, while control group displayed more inflammatory granulation tissue and partially re-epithelialized epidermis with overlying serum crust. Collagen-chitosan film treated wounds demonstrated pale but more mature collagen bundles than the controls. In contrast, collagen-chitosan sheet treated wounds displayed well-organized compact collagen bundles that were oriented parallel to the epidermis. Furthermore, trichrome semi-quantitative analysis revealed significantly increased collagen intensity in collagen-chitosan sheet treated wounds compared to all other wounds ($p<0.05$).

Type IV collagen antibody staining which stains the blood vessels was used to demonstrate the vascularization of each experimental group after 2 weeks of implantation. Higher number of blood vessel/density were observed in the collagen-chitosan sheet/film implanted group than in the control group (A large number of micro-vessels were observed in the collagen-chitosan sheet and film implanted group, and the micro-vessel density was much higher compared with the control group. This finding could be attributed to the presence of bioactive cues in the collagen-chitosan samples along with its porosity improved the activation and facilitated the endothelial cells to form new blood vessels in the wound bed.

We claim:

1. A process for extraction of collagen from fish scale consisting of:
    (i) washing, softening, and depigmenting the fish scale by washing the fish scale with a salt solution selected from NaCl or KCl, followed by depigmenting and further softening the fish scale by treating the washed and softened fish scale with an alkali selected from NaOH or KOH, for 24-48 hours with a shaking speed of 60-100 rpm;
    (ii) subjecting the fish scale obtained in step (i) to crushing and smashing at a temperature up to 20° C. to achieve disintegration through punching, grinding and tearing of the fish scale;
    (iii) treating the fish scale obtained step (ii) with 0.3 M to 0.5 M acetic acid at a temperature of 6° C. to 10° C. with stirring at a shaking speed of 60-100 rpm, thus providing dissolution of collagen directly from the treated fish scale to provide a collagen containing acetic acid solution;
    (iv) carrying out filtration of the collagen containing acetic acid solution obtained in step (iii) to provide a first solution of soluble collagen and a first residue;
    (v) subjecting the first solution of soluble collagen obtained in step (iv) to salt treatment to precipitate collagen from the first solution of soluble collagen, followed by filtration to generate a solution and a second residue;
    (vi) subjecting the second residue obtained in step (v) to acetic acid treatment to provide a second collagen containing solution;
    (vii) carrying out continuous dialysis of the second collagen containing solution obtained in step (vi) by introducing the second collagen containing solution into a reverse osmosis hollow fiber membrane in a dialyzer, wherein dialysate used for the continuous dialysis is water, and controlling inlet and outlet pressure of the second collagen containing solution in the reverse osmosis hollow fiber membrane, wherein the inlet pressure is maintained at 300 to 1000 mbar and the outlet pressure is maintained at 100 to 600 mbar, and wherein an inlet pressure of the dialysate is maintained at 1 to 200 mbar below the outlet pressure in the reverse osmosis hollow fiber membrane; and
    (viii) obtaining purified collagen from an outlet of the dialyzer, the purified collagen having a yield of greater than 22% based on a total fish scale weight basis, and purity of 92-95%.

2. The process as claimed in claim 1, wherein the first residue obtained in step (iv) has collagen content and is subjected to:

i) crushing and smashing;
ii) treating with acetic acid and pepsin;
iii) carrying out filtration to generate a solution of soluble collagen and a residue; and
iv) recycling the solution of soluble collagen to step (v) of claim 1, and the residue to step (ii) of claim 1.

3. The process as claimed in claim 1 step (vii), wherein the continuous dialysis is carried out until the second collagen containing solution has a pH of 5.5 to 6.5.

4. The process as claimed in claim 1 step (ii), wherein the fish scale is subjected to crushing and smashing at a temperature up to 10° C.

* * * * *